(12) United States Patent
Zipper

(10) Patent No.: US 8,887,731 B2
(45) Date of Patent: Nov. 18, 2014

(54) PESSARY DEVICE

(76) Inventor: Ralph Zipper, Melbourne, FL (US)

( * ) Notice: Subject to any disclaimer, the term of this patent is extended or adjusted under 35 U.S.C. 154(b) by 496 days.

(21) Appl. No.: 12/394,085

(22) Filed: Feb. 27, 2009

(65) Prior Publication Data
US 2009/0216071 A1 Aug. 27, 2009

Related U.S. Application Data

(60) Provisional application No. 61/067,266, filed on Feb. 27, 2008.

(51) Int. Cl.
| A61F 6/06 | (2006.01) |
| A61M 29/00 | (2006.01) |
| A61F 2/00 | (2006.01) |
| A61F 6/08 | (2006.01) |

(52) U.S. Cl.
CPC .............. *A61F 2/0009* (2013.01); *A61F 6/08* (2013.01)
USPC ............ 128/834; 128/836; 606/192; 606/193

(58) Field of Classification Search
CPC .................................. A62F 6/08; A62F 2/0009
USPC .................. 128/834, 835, 836; 606/192, 193
See application file for complete search history.

(56) References Cited

U.S. PATENT DOCUMENTS

| 444,513 | A | 1/1891 | Wagner |
| 476,698 | A | 6/1892 | Taylor |
| 525,785 | A | 9/1894 | Hurdle |
| 992,013 | A | 5/1911 | Leyson |
| 1,003,821 | A | 9/1911 | Svejnar |
| 1,382,033 | A | 6/1921 | Wallace |
| 2,769,442 | A | 11/1956 | Stubbs |
| 2,856,920 | A | 10/1958 | Indelicato |
| 5,224,494 | A | 7/1993 | Enhorning |
| 5,611,768 | A | 3/1997 | Tutrone, Jr. |
| 6,470,890 | B1 * | 10/2002 | Diokno et al. ................ 128/885 |
| 2004/0030352 | A1 * | 2/2004 | McGloughlin et al. ....... 606/193 |
| 2008/0183204 | A1 * | 7/2008 | Greenhalgh et al. .......... 606/198 |

OTHER PUBLICATIONS

Anthony J. Viera, LT, MC, USNR, and Margaret Larkins-Pettigrew, LCDR, MC, USNR, Practical Use of Pessary, http://www.aafp.org/afp/20000501/2719.html.
Ranee Thakar and Stuart Stanton, Regular Review: Management of genital prolapse, http://resources.bmj.com/bmj/subscribers.

* cited by examiner

*Primary Examiner* — Victoria J Hicks
(74) *Attorney, Agent, or Firm* — Stephen C. Thomas

(57) ABSTRACT

A pessary having a main stem and an inflatable bladder disposed about the proximal larger diameter section of the main stem. The main stem further provides a distal smaller diameter portion having a cap at its distal tip and a check valve disposed there under. The check valve communicates with a central fluid passage that may extend into the proximal larger diameter section of the main stem. Secondary fluid passages connect the central fluid passage to the inflatable bladder volume disposed about the outer circumference of the proximal larger diameter section of the main stem. The main stem provides support to the pelvic structures and the inflatable bladder acts to hold the device in position. At least one void through the proximal larger diameter portion of the main stem allows bodily material to pass from the vagina through the pessary device thereby decreasing the amount of vaginal discharge.

5 Claims, 4 Drawing Sheets

PESSARY DEVICE

CROSS REFERENCE TO RELATED APPLICATIONS

This application claims the benefit of provisional patent application Ser. No. 61/067,266, filed with the USPTO on Feb. 27, 2008, which is herein incorporated by reference in its entirety.

STATEMENT REGARDING FEDERALLY SPONSORED RESEARCH OR DEVELOPMENT

Not applicable.

INCORPORATION-BY-REFERENCE OF MATERIAL SUBMITTED ON A COMPACT DISK

Not applicable.

BACKGROUND OF THE INVENTION

1. Field of the Invention

The present invention generally relates to an artificial means of supporting the bladder, the rectum, the bowel, the vagina, the urethra, and/or the uterus, more specifically, the present invention relates to a device for treating urinary incontinence, cystoceles, rectoceles, urinary prolapse, and enteroceles.

2. Background Art

Continence, or normal control of urine retention in the bladder, involves the coordination of the bladder, bladder neck and urinary sphincter. The body stores urine in the bladder by maintaining a closed bladder neck and a contracted urinary sphincter muscle. To pass urine the bladder contracts while the bladder neck opens and the urinary sphincter muscle relaxes.

Urinary incontinence (UI) occurs when one or more of the anatomical structures related to urine storage malfunctions and leads to a loss of control of urination. The most common type of incontinence is caused by hypermobility of the bladder neck and urethra due to weakening of the tissues surrounding these structures. In females, pelvic trauma associated with child birth is a common cause of tissue weakening. Another cause of incontinence is a deficiency in urinary sphincter muscle control, intrinsic sphincter deficiency (ISD). It is estimated that approximately 8.5 million women suffer from UI in the United States. Up to 75% of female nursing home patients experience some degree of urinary incontinence, creating a tremendous economic as well as hygienic burden.

Female incontinence is currently treated using behavioral techniques, various devices, surgical techniques, and pharmaceuticals. Among devices widely used for alleviating the above problem, a device, which is known as pessary, is a useful alternative or an adjunctive aid rather than a substitute for gynecological surgery. A pessary is a device, which is inserted into the vagina for controlling uterine prolapse, uterine retrodisplacement, or stress urinary incontinence via contact with the walls of the vagina.

Pelvic organ prolapse is a condition defined by herniation of pelvic organs such as the bladder, rectum, or uterus into the vagina or beyond the vaginal opening. It may also lead to complete eversion of the vagina. Pelvic organ prolapse may be caused by vaginal childbirth, hysterectomy, aging and obesity. Over 70 percent of women will eventually have some degree of pelvic organ prolapse. Symptoms may include profound discomfort, bleeding from protrusion of organs, difficulty and or inability to urinate or defecate, frequency of urination, and urinary incontinence. Pelvic organ prolapse is currently treated only by surgery or with a pessary.

Many vaginal pessary devices are known and are available within the marketplace. Some pessaries are made in the form of rigid (i.e. non-inflatable) rings, dishes, hodges, donuts, and the like. Many of such exemplary devices are produced by Millex Products, Inc., of Chicago, Ill. The aforementioned pessaries are inserted and removed manually, which often presents a problem when insertion and removal is to be performed by the patient. Often the difficulty of insertion and/or removal necessitates insertion or removal by a physician or nurse. Such professionals often also have difficulty with this and significant patient discomfort results. In the past, doctors and nurses would fit the patient with a type of pessary, insert it into the patient's vagina where it could remain for up to three months. In order to decrease vaginal infection and odor, daily, weekly or semiweekly removal and cleaning is preferred. However, secondary to the difficulty with self-removal and reinsertion and the inconvenience of making semi-monthly trips to the doctor's office, it has become the convention to allow three months without removal. The patient then returns to the doctor's office where the pessary is removed, cleaned and re-inserted (or a new pessary may be substituted). Secondary to the fact that this practice results in significant vaginal discharge, odor and infection, pessaries are seldom used to treat incontinence and pelvic organ prolapse. The majority of patients instead are triaged to surgery.

The new prior art approach is to use the pessary on a daily basis by having the patient manually insert the pessary in the morning and then manually remove the pessary in the evening. When removed, the patient may clean the pessary with special solution and have the pessary ready for manual re-insertion by the patient the next morning. This is the same idea as intermittent catheterization that is now done three-four times per day by the patient rather than having an indwelling Foley catheter in the bladder for usually four weeks where only the doctor inserts and removes the catheter.

The problem with this new method of daily insertion and removal is that the patient is required to learn how to insert and remove the pessary herself. However, as has been mentioned above, the aforementioned rigid pessaries are difficult to insert and likewise, very difficult to remove by the patient alone. There is great variability in the size of the bony pelvis and the surrounding soft tissue between respective patients. To accommodate these rigid pessaries are made in a variety of different sizes, and a pessary cannot be worn if it is improperly sized. If the pessary is too big, it will cause ulceration and discomfort; however, if the pessary is too small, it may fall out or fail to provide the required support. Conventional pessaries are made available in standard sizes. Unfortunately, it has been found that a large number of women fall in the range between these conventionally available pessary sizes and are thereby unable to receive a proper size and fit.

Prior attempts have been made to make an inflatable pessary to correct this problem. Although there are several available inflatable pessaries, they are all plagued by at least two major problems. First, unlike semi-rigid pessaries which may have open channels to allow air flow, inflated pessaries have failed to maintain an open channel to provide air flow. Such a lack of air flow results in copious and malodorous vaginal discharge. Second, existing inflatable pessaries are difficult to inflate and are even more difficult to deflate. Given these inflation and deflation hardships, patients experience great difficulty in removing the pessary prior to cleaning or intercourse and pessary re-insertion thereafter.

As one example, a conventional pessary consists of a donut-type inflatable ring which is manually inserted into the vagina and which is connected via a flexible tube with an externally located pumping bulb. The inflatable donut is individually fitted and adjusted into a required place of the vagina and then is inflated to a proper size by means of the pumping bulb via the flexible tube. The donut is provided with a check valve for maintaining the pessary in an inflated state. Upon completion of inflation, the bulb is disconnected leaving a short piece of the flexible tube protruding out from the vagina, so that this protruding end can then be used for removing the donut pessary from the vagina. Such a device is produced by Millex Products, Inc., of Chicago, Ill. A disadvantage of this device is that it is still manually inserted and that the end of the flexible tube protruding from the vagina creates discomfort and serves as a wick for infection and drainage. An additional disadvantage exists in that the pessary in its inflated state allows no means of ingress and egress of air. This leads to profound and copious vaginal discharge and infection.

U.S. Pat. No. 5,611,768 issued in 1997 to R. Tutrone discloses a pessary device comprising two sequentially arranged inflatable chambers, one of which is placed into the anterior part of the vaginal cavity and another to the posterior part of the vaginal cavity. Both chambers are inflated separately via separate valves located outside the vagina and remaining attached to the device after the inflation. At least one of the chambers is intended for pressing via the vaginal wall on the urethra, thus combating female incontinence.

This device entails the same disadvantages as the previously described pessaries, in that the pessary removal means remains permanently attached to the pessary while in use. Additional disadvantages include the complicated construction of the device, the device's requirement for manual insertion and removal, the lack of a means of ingress and egress of air to decrease vaginal discharge and infection, and the lack of any semirigid or rigid component to provide increased support and resistance to unwanted movement within the vaginal cavity.

The present invention is intended to address these problems associated with the non-surgical treatment of urinary incontinence as well as treatments involving disorders such as pelvic organ prolapse. Pelvic organ prolapse refers to the herniation of the bladder, rectum, bowel, urethra, and/or uterus. This is caused by loss of support from surrounding connective tissue and muscle. Pelvic organ prolapse causes numerous symptoms such as urinary incontinence, obstruction of urination, obstruction of defecation, constipation, pain, bleeding, and problems with intercourse. It is recognized that most women will eventually develop pelvic organ prolapse, and it has been estimated that as many as 7% of these women will undergo surgery for pelvic prolapse. The problems associated with conventional pessaries have resulted in many health care providers electing for surgery without even first attempting treatment with a pessary. Of the women that are treated with a pessary, a significant portion elect surgery rather than dealing with the problems of a pessary including poor fit, pain during removal and insertion (often having to be routinely done by a healthcare provider), and the vaginal discharge that builds up behind the pessary.

The majority of patients that are successfully fit with a pessary are wearing a semi-rigid pessary. Until now, the semi-rigid pessaries have been the best available, but these devices also have significant drawbacks. Patients and physicians often have trouble inserting and removing these semi-rigid pessaries. As a result, sexual intercourse may then be abandoned and the patient may be forced to visit the physician every two to three months to have the pessary removed and cleaned by the healthcare provider. Removal is often quite painful for the patient and may even cause bleeding.

The balance that a pessary requires and which the prior art fails to achieve is a pessary which is small enough to be inserted and removed comfortably, large enough to stay in place during activity, rigid enough to allow air tunnels to remain open, and soft enough to not cause trauma or discomfort during use. Such a device is provided for by the present invention.

BRIEF SUMMARY OF THE INVENTION

In one embodiment of the present invention, a pessary device comprising a main stem comprising a distal smaller diameter section and a proximal larger diameter section, a central fluid passage disposed within the main stem, a check valve disposed within the central fluid passage, an inflatable bladder disposed about the outer circumference of the larger diameter section of the main stem, the inflatable bladder defining an inflatable bladder volume, and at least one secondary fluid passage providing fluid communication between the central fluid passage and the inflatable bladder volume.

One aspect of the present invention is to provide a pessary which may fit and conform to a plurality of women with each respective woman having a different pelvic shape and size.

It is another aspect of the present invention to provide a pessary which may have at least one rigid or semi-rigid portion and at least one inflatable portion.

It is another aspect of the present invention to provide a pessary which may easily be inflated by the patient or the health care provider while the pessary is in the vagina.

It is another aspect of the present invention to provide a pessary which may easily be removed by the patient or the health care provider.

It is another aspect of the present invention to provide a pessary that coincidentally deflates as the patient attempts to remove the device.

It is another aspect of the present invention to provide a pessary having an inflatable ring that causes less discharge and odor than entirely inflatable pessaries in the art.

It is another aspect of the present invention to provide a pessary that does not require frequent trips to the physician or other health care provider.

It is another aspect of the present invention to provide a pessary that does not discourage intercourse.

It is another aspect of the present invention to provide an improved non-surgical option for the treatment of pelvic prolapse, urinary incontinence, cystoceles, rectoceles, and enteroceles.

DETAILED DESCRIPTION OF THE INVENTION

Figure 1:
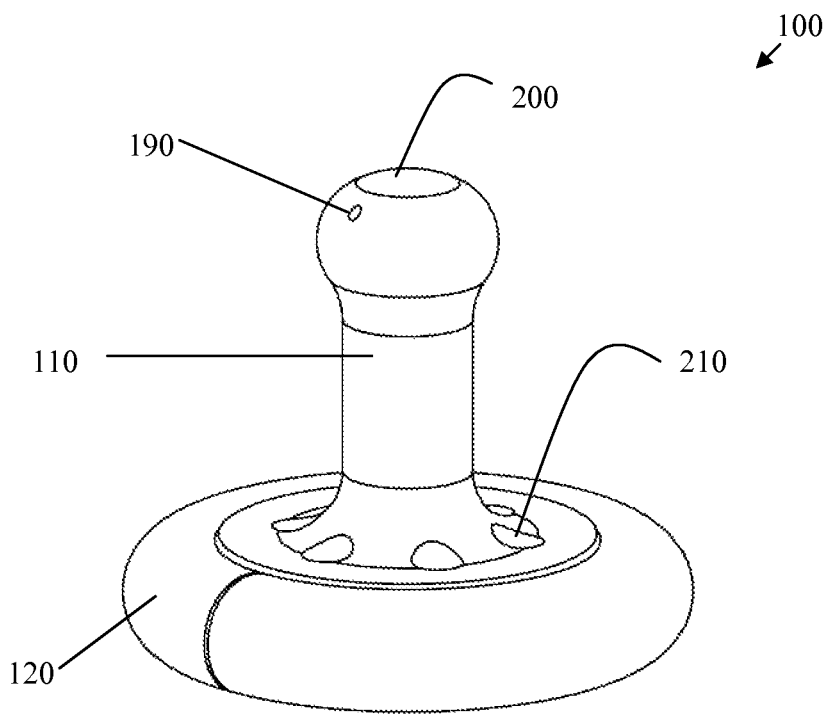
FIG. 1 depicts a perspective view of an embodiment of a pessary of the present invention.
Figure 2:
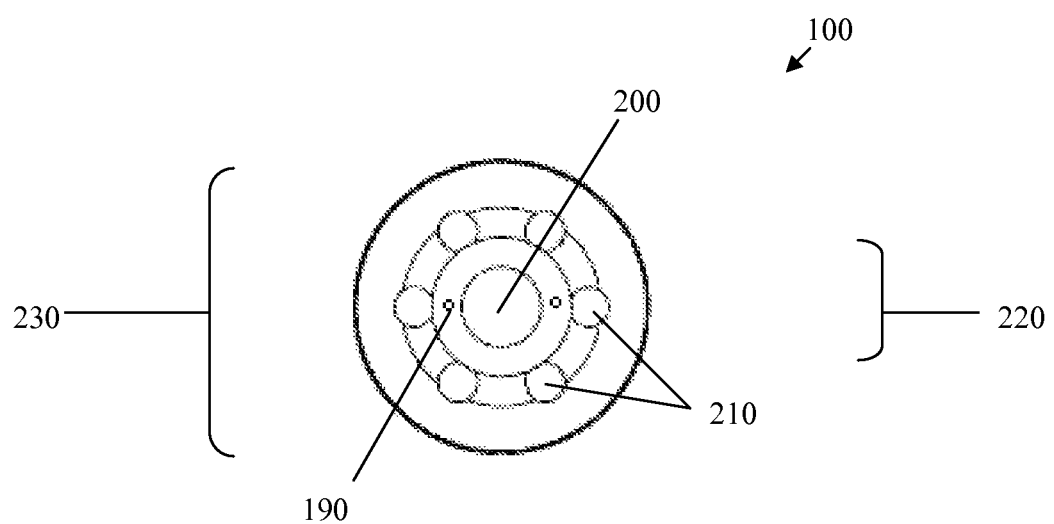
FIG. 2 depicts a top planar view of an embodiment of a pessary of the present invention.

The invention disclosed herein is an improved inflatable pessary wherein one embodiment within the scope of the present invention is generally depicted in FIGS. 1-7. The present inventive inflatable pessary 100 may comprise a main stem 110 having a distal smaller diameter section 220 and a proximal larger diameter section 230, an inflatable bladder 120 disposed about the outer circumference of the proximal larger diameter section 230, a plug 130, a check valve 140 axially disposed within the distal smaller diameter section 220, a main central passage 150 axially spanning between the distal smaller diameter section 220 and the proximal larger diameter section 230, an inflatable bladder volume 170 defined by the inflatable bladder 120, at least one secondary fluid passageway 160 connecting the main central passage 150 to the inflatable bladder volume 170, a deflation nipple 180 disposed at the distal end of the main stem 110, at least one vent port 190 allowing for deflation and the exit of fluid or gas from the pessary device 100, a cap 200, and at least one passageway 210 disposed through the proximal larger diameter portion 230 providing for flow of bodily material there through.

Within the scope of the present invention, any fluid or gas such as water, saline, air, and the like may be used as the chosen medium to inflate and deflate the inflatable bladder of the present inventive device. While certain embodiments may reference a specific inflation medium, it is understood within the scope of the present invention that fluid, liquid, gas, water, saline, air, and the like are all freely interchangeable within the context of the present invention and any described embodiments are not to be so literally limited to any one specifically referenced inflation medium. In the present invention, the term "fluid" means any known fluid, liquid, or gas including but not limited to water, saline, air, and the like.

The present inventive inflatable pessary 100 may be manually inserted and removed from the patient's vagina without the use of any specialized insertion or removal tools as is typically required in the prior art. When properly installed, the entire inflatable pessary device 100 may be located within the patient's vagina. The inflatable pessary 100 may have a predominately mushroom-shape provided by the main stem's 110 distal smaller diameter section 220 and the proximal larger diameter section 230 having an inflatable bladder 120 disposed around its outer circumference. The present inventive pessary 100 is a combination of both rigid or semi-rigid components and an inflatable component. The rigid or semi-rigid main stem 110 provides stability of form and shape to the pessary 100 while also providing substantial support for surrounding pelvic structures. The inflatable bladder 120 disposed about the outer circumference of the proximal larger diameter section 230 functions to hold the pessary 100 inside the vagina and keep the device in its desired location. The proximal larger diameter portion 230 also comprises a section below its outer inflatable edge that may also be rigid or semi-rigid. At least one passageway 210 may be disposed through the rigid or semi-rigid portion of the proximal larger diameter portion 230 to allow for ingress and/or egress of any bodily material which may include solids, liquids, or gases through the pessary 100. The at least one passageway 210 serves to alleviate the development of copious malodorous vaginal discharge associated with conventional pessaries.

Figure 3:
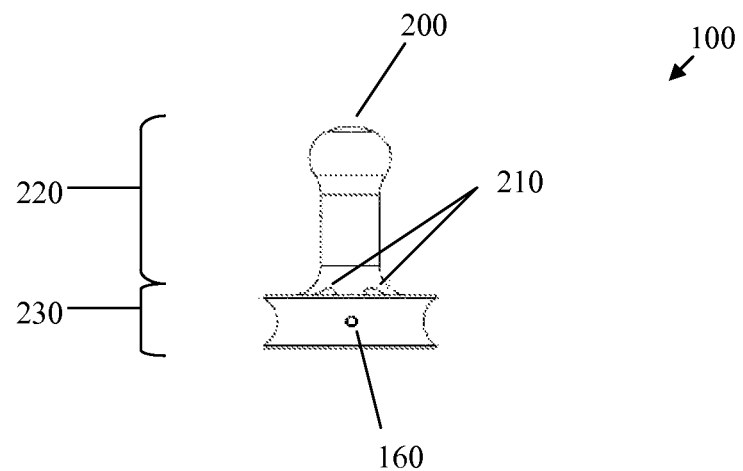
FIG. 3 depicts a side view of an embodiment of a pessary of the present invention (shown at manufacturing stage without attached inflatable member).
Figure 4:
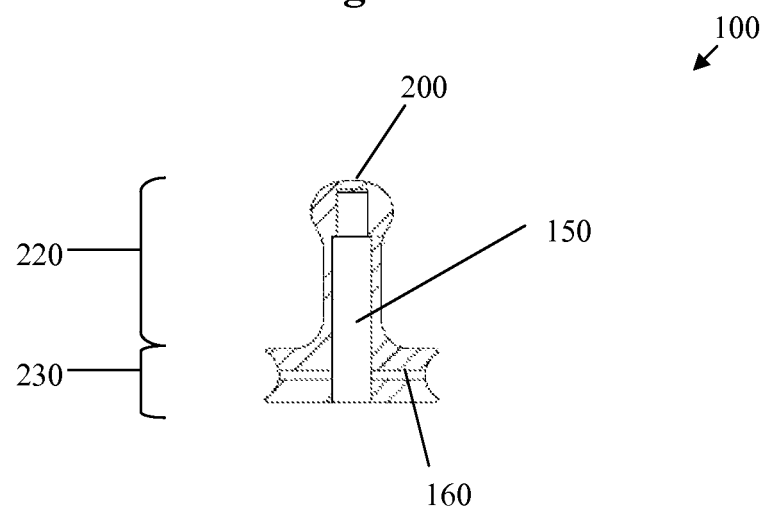
FIG. 4 depicts a side sectional view of an embodiment of a pessary of the present invention (shown at manufacturing stage without attached inflatable member).
Figure 5:
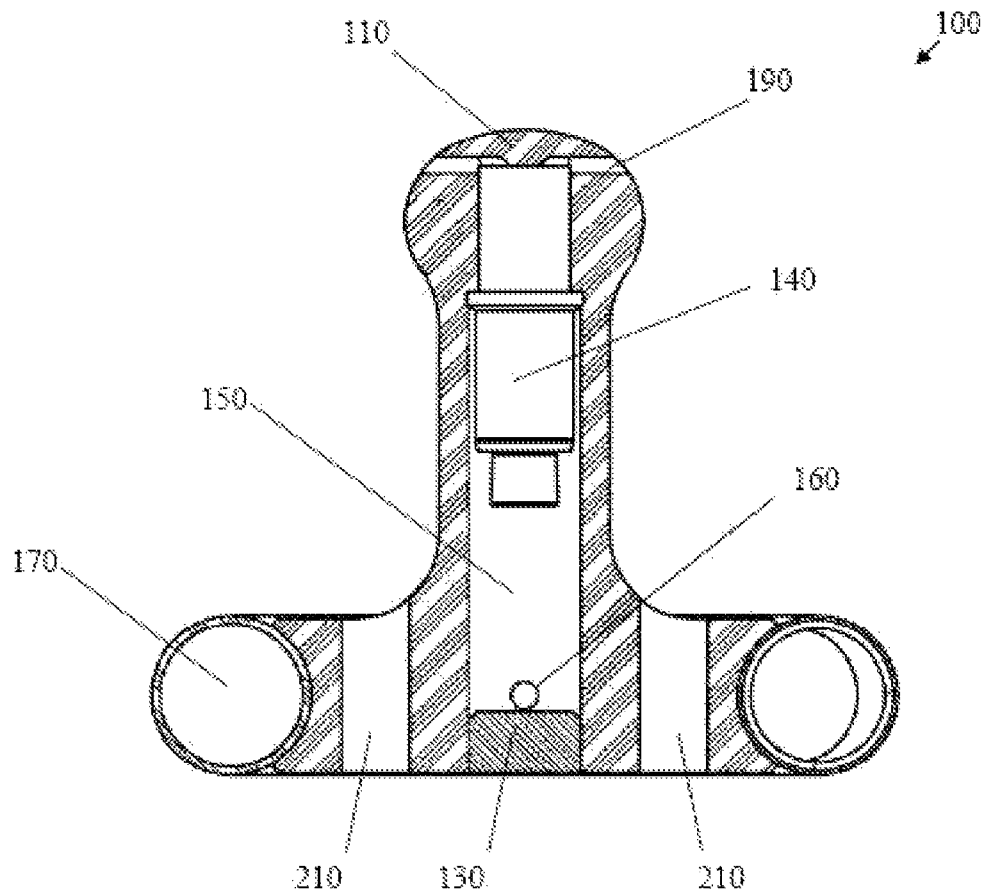
FIG. 5 depicts another side sectional view of an embodiment of a pessary of the present invention (shown with attached inflatable member).
Figure 6:
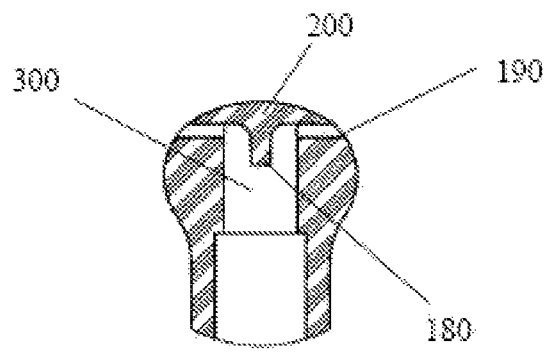
FIG. 6 depicts a zoomed in side sectional view of an embodiment of the main stem tip of a pessary of the present invention.

As depicted in FIGS. 3-5, the main stem 110 comprises a distal smaller diameter section 220 at its distal end pointing toward the vaginal exit when properly positioned within a patient. The distal smaller diameter portion 220 may be rigid or semi-rigid and have a check valve 140 disposed therein allowing for both inflation and deflation of the inflatable bladder volume 170 via fluid communication between the central fluid passage 150 and the at least one secondary fluid passage 160 and the inflatable bladder volume 170. The check valve 140 may be replaced with any valve means known within the art capable of controlling fluid passage. The distal smaller diameter section 220 may contain at least one channel (e.g. the central fluid passage 150) throughout its entirety to allow fluid to move in and out of the inflatable bladder 120 of the pessary 100 and thereby allowing for placement, inflation, adjustment, deflation, and removal of the pessary 100 as needed.

The inflatable bladder 120 disposed about the circumference of the proximal larger diameter section 230 may serve at least three functions. First, insertion of the pessary 100 may be greatly improved since the inflatable bladder 120 may be deflated prior to insertion and then inflated after the pessary 100 has been disposed inside the vagina, allowing for one size pessary to fit a plurality of women and provide each with a unique customized fit due to its infinitely inflatable adjustments. The inflatable bladder 120 also provides a softer cushion interface against the surrounding vaginal and uterine tissues, as compared to conventional pessaries. While providing a gentler interface, the inflatable bladder 120 still remains rigid enough to provide the required support to the surrounding pelvic structures. The rigid or semi-rigid main stem 110 may provide such support and further strengthens the inflatable bladder 120 disposed there around. The inflatable bladder 120 may further be inflated or deflated to either facilitate comfortable adjustment in use or removal of the pessary 100 from the patient as necessary. The inflation may also be titrated to achieve adequate pressure and support beneath the urethra to achieve urinary continence. In a preferred embodiment, the inflatable bladder 120 and the inflatable bladder volume 170 that it defines may be torus or donut-shaped. However, the inflatable bladder 120 may comprise any cross sectional shape provided that the inflatable bladder 120 assists in maintaining the pessary 100 in its proper anatomical position within the patient.

The distal smaller diameter section 220 of the main stem 110 may be utilized to carry out both the inflation and deflation steps for the pessary device 100. When disposed within a patient, pressure can be manually applied to the inflatable bladder 120 disposed about the proximal larger diameter section 230 simply by pulling on the distal smaller diameter section 220 of the main stem 110 wherein the surrounding pelvic structures increase compression on the inflatable bladder 120. To facilitate such manual manipulation of the pessary device 100 by the user, the distal end of the distal smaller diameter section 220 may comprise a bulbous configuration as shown in FIGS. 1-7. When a user depresses the cap 200, the deflation nipple 180 disposed on the proximal surface of the cap 200 may physically interface with engage the check valve 140 is in an open position. The combination of the deflection of the rigid or semi-rigid main stem 110 and pressure from surrounding pelvic structures being applied to the inflatable bladder 120 while the cap 200 is depressed and traction is being placed on the bulbous member to facilitate removal may initiate deflation of the inflatable bladder 120 as fluid or gas within the inflatable bladder 120 moves through at least one secondary fluid passage 160 and the central fluid passage 150 and is then expelled from the pessary 100. Such an act of deflation of the inflatable bladder 120 of the pessary 100 allows the pessary 100 to be more easily, efficiently, and comfortably removed from the patient by either the patient or health practitioner.

Figure 7:
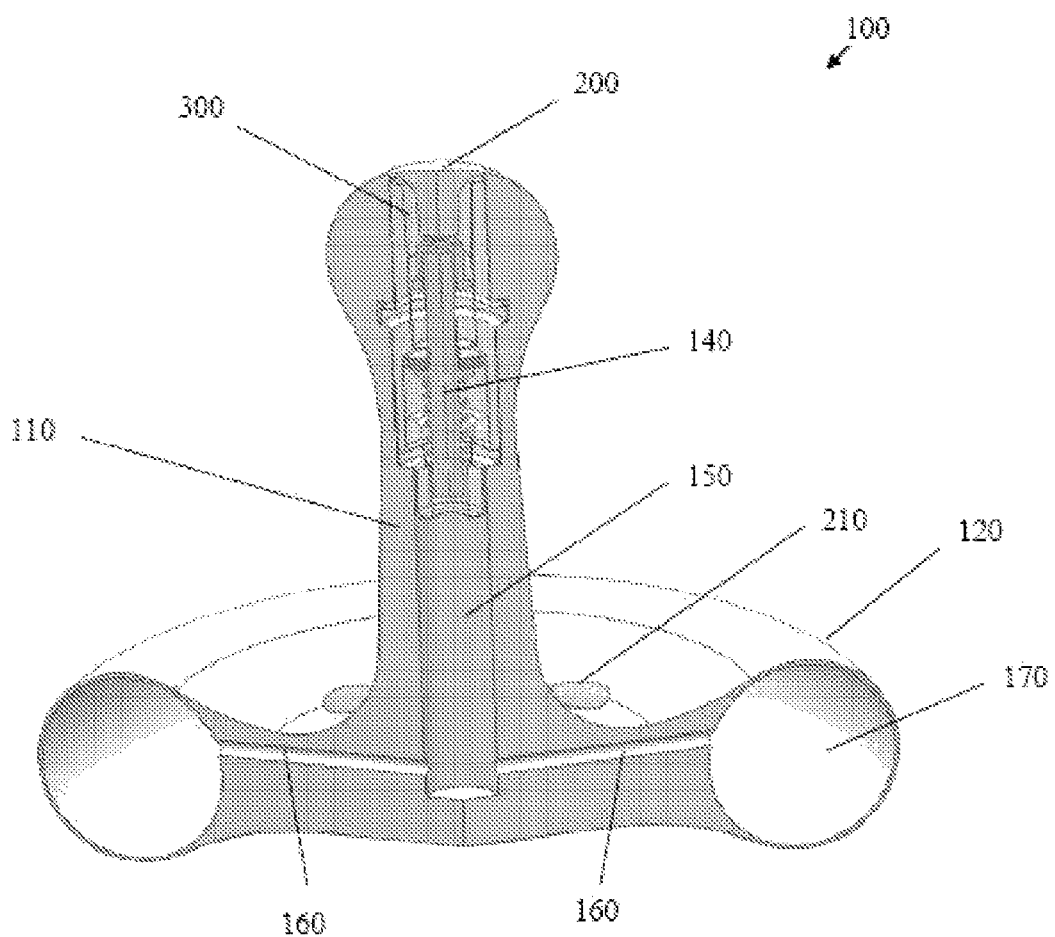
FIG. 7 depicts a perspective sectional view of an embodiment of a pessary of the present invention.

As depicted in FIG. 5, the plug 130 may be necessary to seal the proximal end of the central fluid passage 150 after the insertion of the check valve 140 during manufacture. With the check valve 140 properly disposed in the central fluid passage 150, the proximal end of the central fluid passage 150 may then have a fluid tight seal via insertion of the plug 130. If another form of manufacture of the main stem 110 is utilized and incorporates a different means of inserting the check valve 140 into the central fluid passage 150 of the pessary device 100, the plug 130 location may then comprise a unitary proximal wall of the main stem 110 within the proximal larger diameter section 230, as shown in FIG. 7.

In use, a pessary 100 of the present invention may first occupy a deflated state to facilitate its insertion into vagina of a patient. With the pessary 100 properly disposed entirely within the patient's vagina, inflation of the pessary 100 may then proceed. In a preferred embodiment, the cap 200 may provide a removable covering that may be hingedly connected to the distal end of the distal smaller diameter section 220 of the rigid or semi-rigid main stem 110. With the cap 200 hinged back or otherwise removed, an access port may be exposed at the distal end of the distal smaller diameter section 220 of the pessary device 100. Such an access port may provide for a point of communication between the pessary device 100 and standard Luer fittings, conventional I.V. tubing, and/or conventional syringes. Fluid or gas that may be input through the access port may comprise any fluids or gases known within the art including but not limited to water, saline, air and the like. The inflatable bladder 120 may be inflated to any customizable level sufficient to stabilize the pessary 100 in the proper location within the unique pelvic structure of the patient. During inflation, fluid or gas is advanced into the pessary 100 through the access port and central fluid passage 150. After passing through the check valve 140, the inflating fluid or gas may then travel into the central fluid passage 150 and thereafter into the adjacent at least one secondary fluid passage 160 (see FIGS. 4, 5 and 7). The at least one secondary fluid passage 160 serves to connect the central fluid passage 150 to the inflatable bladder volume 170. To more properly customize and fit the pessary 100 to the respective patient, the inflatable bladder 120 may be inflated to its necessary functional volume while the pessary 100 is entirely disposed within the vagina of the patient.

After inflation is complete, the cap 200 may be hinged closed or otherwise closed and re-seated flush with the distal tip of distal smaller diameter section 220 of the main stem 110. At any time after pessary 100 insertion and inflation, the cap 200 may again be hinged open or otherwise removed to regain access to the access port and/or check valve 140 for performing any necessary adjustments to the inflation level and/or positioning of the pessary 100.

Preferably, to facilitate removal of the pessary device 100 deflation of the present inventive pessary 100 may first occur. To initiate deflation of the inflatable bladder 120 of the pessary 100, the doctor or patient may grasp the bulbous configuration at the distal end of the main stem 110 and depress the cap 200 while simultaneously gently pulling the pessary 100 toward the exit of the vagina. Depression of the cap 200 causes the deflation nipple 180, a protrusion disposed on the proximal surface of the cap 200, to physically interface with a spring loaded post of the check valve 140 causing the fluid or gas (possibly pressurized) within the central fluid passage 150, at least one secondary passage 160, and inflatable bladder 120 to escape the pessary device 100 via the at least one vent port 190. The at least one vent port 190 provides an exit pathway for fluid being released from the pessary device 100. Deflection of the main stem 110 and increased surrounding pelvic tissue pressure as the doctor or patient gently pulls the device 100 towards the vaginal exit further facilitate deflation of the inflatable bladder volume 170. Due to its unique and beneficial configuration, the pessary 100 of the present invention may be removed without the need or use of any additional devices or tools.

While the above description contains much specificity, these should not be construed as limitations on the scope of any embodiment, but as exemplifications of the presently preferred embodiments thereof. Many other ramifications and variations are possible within the teachings of the various embodiments.

Thus the scope of the invention should be determined by the appended claims and their legal equivalents, and not by the examples given.

What is claimed is:

1. A pessary device comprising:
    a main stem comprising a distal smaller diameter section and a proximal larger diameter section having an outer circumference, wherein said outer circumference of said proximal larger diameter section of said main stem is concave in shape;
    a central fluid passage disposed within said main stem;
    a check valve disposed within said central fluid passage;
    a cap attached to a distal end of said distal smaller diameter section of said main stem, said cap providing a removable covering for said check valve disposed within said central fluid passage when said pessary device is in use, wherein said cap is hingedly attached to said distal end of said distal smaller diameter section;
    an inflatable bladder disposed about said outer circumference of said proximal larger diameter section of said main stem adapted to contain a fluid, said inflatable bladder comprising a torus-shape and further defining an inflatable bladder volume;
    at least one secondary fluid passage providing fluid communication between said central fluid passage and said inflatable bladder volume;
    a deflation nipple disposed on a proximal surface of said cap and projecting toward said check valve, wherein depression of said cap causes said deflation nipple to physically interface with said check valve thereby allowing said fluid to exit from said pessary device;
    at least one vent port disposed within said distal smaller diameter section of said main stem, said at least one vent port providing an exit pathway for said fluid to exit said pessary device;
    an access port disposed at the distal end of said distal smaller diameter section of said main stem, wherein said access port provides for a point of communication between said pessary device and a syringe or surgical tubing allowing for input of said fluid into said central fluid passage, said at least one secondary fluid passage, and said inflatable bladder of said pessary device;
    wherein said cap covers said access port when said access port is not in communication with said syringe or said surgical tubing; and
    wherein said distal end of said distal smaller diameter section of said main stem is capable of facilitating user manual manipulation of said pessary device.

2. The pessary device of claim 1, wherein said distal smaller diameter section of said main stem further comprises a bulbous configuration.

3. The pessary device of claim 1, wherein said proximal larger diameter section comprises at least one passageway disposed through said proximal larger diameter section allowing for passage of bodily material through said pessary device parallel to a longitudinal axis of said main stem such that said bodily material can be discharged from a vagina of a user through said at least one passageway.

4. A pessary device comprising:
a main stem comprising a distal smaller diameter section and a proximal larger diameter section having an outer circumference, wherein said proximal larger diameter section comprises at least one passageway disposed through said proximal larger diameter section allowing for passage of bodily material through said pessary device parallel to a longitudinal axis of said main stem such that said bodily material can be discharged from a vagina of a user through said at least one passageway;
a central fluid passage disposed within said main stem;
a check valve disposed within said central fluid passage;
a cap attached to a distal end of said distal smaller diameter section of said main stem, said cap providing a removable covering for said check valve disposed within said central fluid passage when said pessary device is in use, wherein said cap is removably attached to said distal end of said distal smaller diameter section, and wherein said cap remains removably attached to said distal end of said distal smaller diameter section when said pessary is in use;
an inflatable bladder disposed about the outer circumference of said proximal larger diameter section of said main stem, said inflatable bladder defining an inflatable bladder volume adapted to contain a fluid;
at least one secondary fluid passage providing fluid communication between said central fluid passage and said inflatable bladder volume;
a deflation nipple disposed on a proximal surface of said cap and projecting toward said check valve, wherein depression of said cap causes said deflation nipple to physically interface with said check valve thereby allowing said fluid to exit said pessary device; and
at least one vent port disposed within said distal smaller diameter section of said main stem, said at least one vent port providing an exit pathway for said fluid to exit said pessary device.

5. The pessary device of claim 4, wherein said distal end of said distal smaller diameter section of said main stem comprises a bulbous configuration capable of facilitating user manual manipulation of said pessary.

\* \* \* \* \*